US009414807B2

(12) United States Patent
Hamada et al.

(10) Patent No.: US 9,414,807 B2
(45) Date of Patent: Aug. 16, 2016

(54) ULTRASOUND DIAGNOSIS APPARATUS, MEDICAL IMAGE DISPLAY APPARATUS AND MEDICAL IMAGE DISPLAYING METHOD

(75) Inventors: Kenji Hamada, Tochigi-ken (JP); Yoshitaka Mine, Tochigi-ken (JP); Itsuki Kuga, Tochigi-ken (JP); Eiichi Shiki, Tochigi-ken (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 347 days.

(21) Appl. No.: 12/691,186

(22) Filed: Jan. 21, 2010

(65) Prior Publication Data
US 2010/0185094 A1 Jul. 22, 2010

(30) Foreign Application Priority Data

Jan. 21, 2009 (JP) ................................. 2009-011177

(51) Int. Cl.
*A61B 8/14* (2006.01)
*G06T 19/00* (2011.01)
(Continued)

(52) U.S. Cl.
CPC . *A61B 8/14* (2013.01); *A61B 6/466* (2013.01); *A61B 8/483* (2013.01); *A61B 8/523* (2013.01); *G06T 19/003* (2013.01)

(58) Field of Classification Search
CPC .......... A61B 6/466; A61B 8/14; A61B 8/483; A61B 8/523; G06T 19/003
USPC .................. 600/437, 443; 382/128
See application file for complete search history.

(56) References Cited

U.S. PATENT DOCUMENTS 6,343,936 B1 * 2/2002 Kaufman et al. ............. 434/262
7,102,634 B2 * 9/2006 Kim et al. ..................... 345/419
(Continued)

FOREIGN PATENT DOCUMENTS

JP 11-56832 3/1999
JP 2005-110973 4/2005
(Continued)

OTHER PUBLICATIONS

English translation of JP 2005-110973 provided by IPDL.*
(Continued)

Primary Examiner — Katherine Fernandez
(74) Attorney, Agent, or Firm — Oblon, McClelland, Maier & Neustadt, L.L.P.

(57) ABSTRACT

An ultrasound diagnosis system, a medical image display apparatus and displaying method that simultaneously acquires virtual endoscopy image data and multi-planar-reconstruction (MPR) image data of a diagnosing target region based on the volume data acquired from an object. Virtual endoscopy image data is generated by setting up a viewing point and a viewing direction on a volume data acquired from the object. A marker is provided on a target region of a lumen organ shown in the virtual endoscopy image data for setting up an observing direction. A reference line started from the volume data is set up along an observing direction. By comparing a voxel value of the volume data that is crossing to the reference line with a prescribed threshold value, a reference point where a surface of the diagnosing target region crosses the reference line is set up to the volume data. MPR image data is generated by extracting each voxel of the volume data corresponded to each of three MPR cross-sectional planes that are mutually orthogonally crossing at the reference point and displayed with the virtual endoscopy image data.

10 Claims, 12 Drawing Sheets

(51) Int. Cl.
*A61B 6/00* (2006.01)
*A61B 8/08* (2006.01)

(56) References Cited

U.S. PATENT DOCUMENTS

| 7,223,240 B2* | 5/2007 | Murashita | 600/443 |
| 8,023,710 B2* | 9/2011 | Summers et al. | 382/131 |
| 2005/0261550 A1* | 11/2005 | Akimoto et al. | 600/117 |

FOREIGN PATENT DOCUMENTS

| JP | 2006-519631 | 8/2006 |
| JP | 2006-346177 | 12/2006 |
| JP | 2008-148858 | 7/2008 |
| JP | 2008-200441 | 9/2008 |

OTHER PUBLICATIONS

Office Action issued May 10, 2013 in Japanese Application No. 2009-011177 (With English Translation).

* cited by examiner

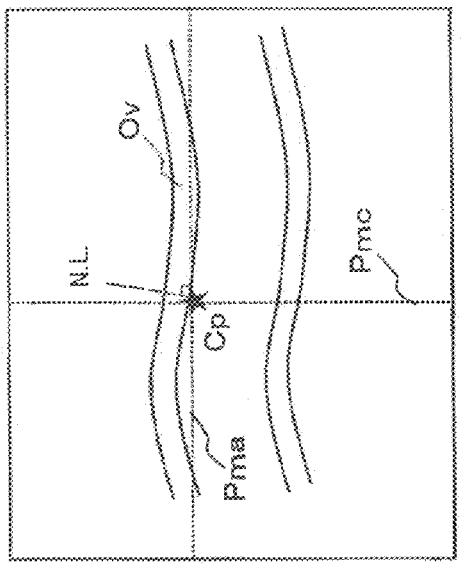
FIG. 9A Ima
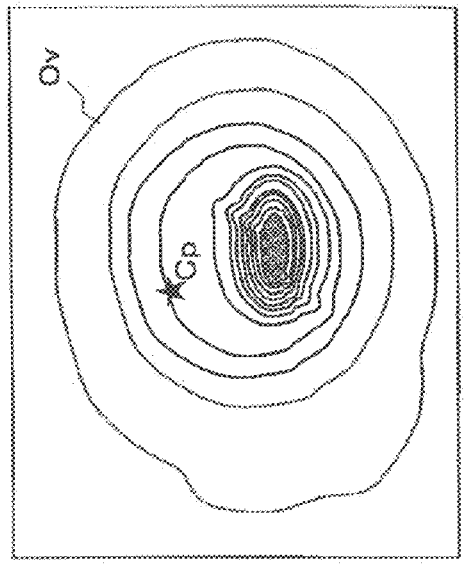
FIG. 9B Imb
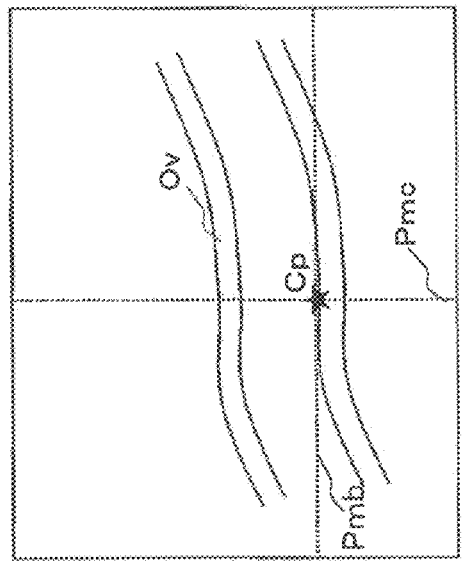
FIG. 9C Imc
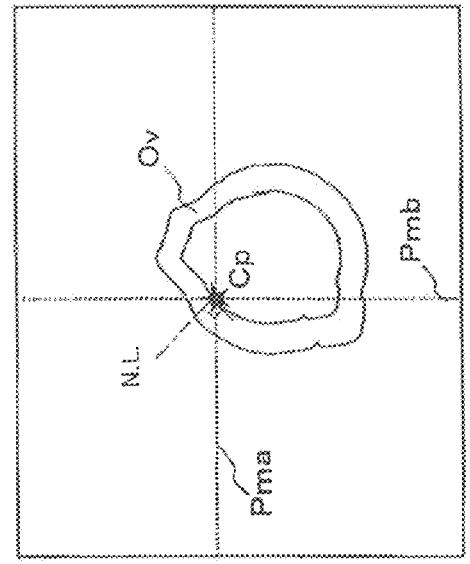
FIG. 9D Ive

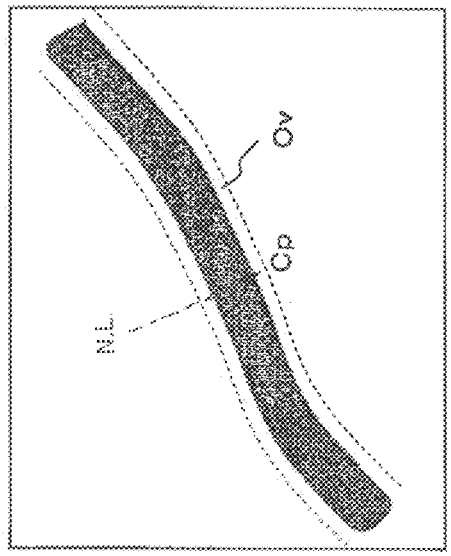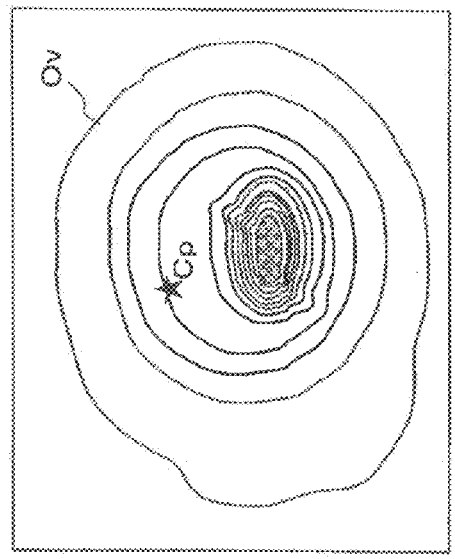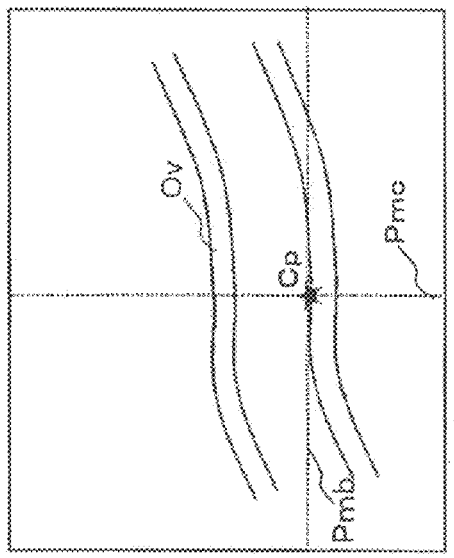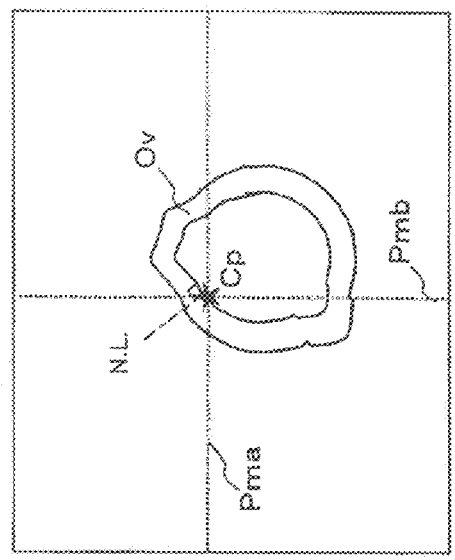

ULTRASOUND DIAGNOSIS APPARATUS, MEDICAL IMAGE DISPLAY APPARATUS AND MEDICAL IMAGE DISPLAYING METHOD

This application claims priority under 35 U.S.C. §119(a) from, and the benefit of, Japanese Patent Application No. 2009-11177, filed on Jan. 21, 2009, the contents of which are expressly incorporated herein by reference in their entirety.

BACKGROUND OF THE INVENTION

1. Field of the Invention

The present invention relates to an ultrasound diagnosis apparatus, a medical image display apparatus and a medical image displaying method, and more particularly, to an ultrasound diagnosis apparatus, a medical image display apparatus and a medical image displaying method that can generate and display virtual endoscopy (fly-through) image data based on three dimensional (3D) image data (hereinafter, "volume data") acquired by performing 3D scans over a target organ in an object.

2. Background of the Invention

An ultrasound diagnosis apparatus transmits and receives ultrasound through a plurality of ultrasound transducers installed in a tip portion of an ultrasound probe to and from a diagnosing target region in an object. By simply touching an ultrasound probe to a patient's body surface, image data of the target region is generated. The generated image data can be displayed on a monitor in real time. An ultrasound diagnosis apparatus is widely used as an apparatus for diagnosing the status of various target organs in a patient's body.

Volume data can be acquired by moving one dimension (1D) array transducers in a direction orthogonal to a direction of the array or by using a two-dimensional (2D)-array ultrasound probe. The 2D array ultrasound probe includes a plurality of transducers arranged both in azimuth and the elevation directions. Recently, it has become possible to improve operability of an ultrasound examination by generating 3D image data and multi-planar reconstruction image data (hereinafter, "MPR image data") by using the volume data acquired in 3D scans over a target organ in an object.

Further, it has recently been proposed to set a virtual viewing point of an observer in a follow organ of the volume data acquired by performing 3D scans on an object in order to examine an inner surface of the follow organ, such as a blood vessel, observed from the viewing point as a virtual endoscopy ("fly-through") image data (For example, see Japanese Patent Application Publication 2005-110973).

According the proposed method, it becomes possible to generate endoscopy image data based on volume data acquired from outside of an object without inserting an endoscope into a body of the object. Consequently, the virtual endoscopy ("fly-through") image data can significantly reduce invasive danger to the object during examination. Further, since it becomes possible to freely set a viewing point or a viewing direction to a follow (lumen) organ such as an alimentary canal or a blood vessel, the proposed method can safely perform examinations of thin follow organs in a high accuracy.

However, according to the proposed method, it has become possible to observe only surface status of the lumen organ by using endoscopy image data acquired through an endoscope. Thus, it has been impossible for the proposed method to examine internal tissue status of a target follow organ. Thus, the conventional fly-through method can not accurately grasp infiltration degrees or invasion degrees of an internal status of a diagnosing target wall of a lumen organ. To accurately grasp infiltration degrees or invasion degrees of an internal status of a diagnosing target wall of a lumen organ is very important for a disease stage examination of a malignant tumor.

SUMMARY OF THE INVENTION

The present invention addresses the above-mentioned and other problems and drawbacks, in order to provide a novel ultrasound diagnosis apparatus, a medical image display apparatus and a medical image displaying method that can simultaneously acquire virtual endoscopy image data and multi-planar-reconstruction (MPR) image data of a diagnosing target region based on volume data acquired from an object.

One aspect of the ultrasound diagnosis system consistent with the present invention is an ultrasound diagnosis apparatus configured to generate virtual endoscopy image data based on volume data acquired through 3D scans over a diagnosing target region in an object, the ultrasound diagnosis apparatus comprising:

a viewing point/direction setting unit configured to set a viewing point and a viewing direction to the volume data;

a virtual endoscopy image data generating unit configured to generate virtual endoscopy image data by processing the volume data based on the viewing point and the viewing direction;

a reference point setting unit configured to set a reference point on the diagnosing target region of the volume data based on the virtual endoscopy image data;

a multi-planar-reconstruction (MPR) plane setting unit configured to set at least one MPR cross-sectional plane to the volume data based on the reference point;

an MPR image data generating unit configured to generate MPR image data based on the volume data on the MPR cross-sectional plane; and a display unit configured to display both the virtual endoscopy image data and the MPR image data.

Another aspect of the present invention is a medical image display apparatus configured to generate and display virtual endoscopy image data based on volume data acquired through 3D scans by using a medical image diagnosis apparatus, the medical image display apparatus comprising:

a volume data storing unit configured to store the volume data;

a viewing point/direction setting unit configured to set a viewing point and a viewing direction to the volume data;

a virtual endoscopy image data generating unit configured to generate virtual endoscopy image data by processing the volume data based on the viewing point and the viewing direction;

a reference point setting unit configured to set a reference point on the diagnosing target region of the volume data based on the virtual endoscopy image data;

a multi-planar-reconstruction (MPR) plane setting unit configured to set at least one MPR cross-sectional plane to the volume data based on the reference point;

an MPR image data generating unit configured to generate MPR image data by extracting a voxel value of the volume data on the MPR cross-sectional plane; and a display unit configured to display both the virtual endoscopy image data and the MPR image data.

A further aspect of the present invention is a medical image displaying method configured to generate and display virtual endoscopy image data based on volume data acquired through 3D scans by using a medical image diagnosis apparatus, the medical image displaying method comprising:

storing the volume data;

setting a viewing point and a viewing direction to the volume data;

generating virtual endoscopy image data by processing the volume data based on the viewing point and the viewing direction;

setting a reference point on the diagnosing target region of the volume data based on the virtual endoscopy image data;

setting at least one MPR cross-sectional plane to the volume data based on the reference point;

generating MPR image data by extracting voxels of the volume data on the MPR cross-sectional plane; and displaying both the virtual endoscopy image data and the MPR image data.

According to the present invention, it becomes possible to set a diagnosis target position on a virtual endoscopy image based on the volume data and to display MPR image included the diagnosis target position. Consequently, it becomes possible to significantly increase diagnosis accuracy and diagnosis efficiency.

BRIEF DESCRIPTION OF THE DRAWINGS

The accompanying drawings, which are incorporated in and constitute part of this specification, illustrate various embodiments and/or features of embodiments of the present invention, and together with the description, serve to explain embodiments of the present invention. Where possible, the same reference number will be used throughout the drawings to describe the same or like parts. In the drawings:

FIG. 9A illustrates an MPR image data Ima of a diagnosing target region of a blood vessel generated on the MPR cross-sectional plane Pma shown in FIG. 8.

FIG. 9B illustrates the MPR image data Imb of the blood vessel generated on the MPR cross-sectional plane Pmb shown in FIG. 8.

FIG. 9C illustrates the MPR image data Imc of a cross-sectional view of the blood vessel on the MPR cross-sectional plane Pmc shown in FIG. 8 generated along a normal line to a surface of the from the reference point Cp shown in FIG. 9B.

FIG. 9D illustrates the displayed virtual endoscopy image data Iye of the blood vessel.

FIG. 10A illustrates the MPR image data Ima of a target region of a blood vessel generated on the MPR cross-sectional plane Pma of.

FIG. 10B illustrates the cavity image data Icy of a blood vessel.

FIG. 10C illustrates a cross-sectional view Imc of the blood vessel generated on the MPR Pmc along a normal line to the surface of the blood vessel from the reference point Cp in the cavity image shown in FIG. 10B.

FIG. 10D illustrates the virtual endoscopy image data Iye of the blood vessel.

DESCRIPTION OF THE EMBODIMENTS

Firstly, an ultrasound diagnosis apparatus consistent with the present invention generates virtual endoscopy image data by setting a viewing point and a viewing direction (i.e., a central direction of a viewing scope). By providing a marker on a diagnosing target region of a follow organ (e.g., a malady portion such as a tumor) displayed in the virtual endoscopy image data. Then, a reference line is set to the observing direction of the volume data used for the generation of the virtual endoscopy image data as an starting point from the viewing point. By comparing a voxel value of volume data crossing with the reference line and a prescribed threshold value for a voxel detection, a reference point is set to the volume data at a point where a surface of a diagnosing target region displayed by the virtual endoscopy image data crosses the reference line. By extracting the voxel of the volume data corresponding to at least one orthogonally crossing MPR plane that crosses at the reference point, at least one MPR image data is generated and displayed together with the virtual endoscopy image data.

In the following description of the embodiments consistent with the present invention, it is supposed that volume data is generated based on 3D B-mode data acquired through 2D (i.e., an azimuth direction and an elevation direction) array ultrasound probes, and a plurality of MPR image data is generated by extracting each voxel of the volume data corresponding to mutually orthogonal three MPR cross-sectional planes. Each of the MPR image data is displayed together with the virtual endoscopy image data. virtual endoscopy image data and MPR image data are generated by using the volume data. Of course, the volume data can be generated by mechanically moving 1D array ultrasound probes. It is further possible to generate the volume data based on another ultrasound data, such as color Doppler data.

Figure 1:
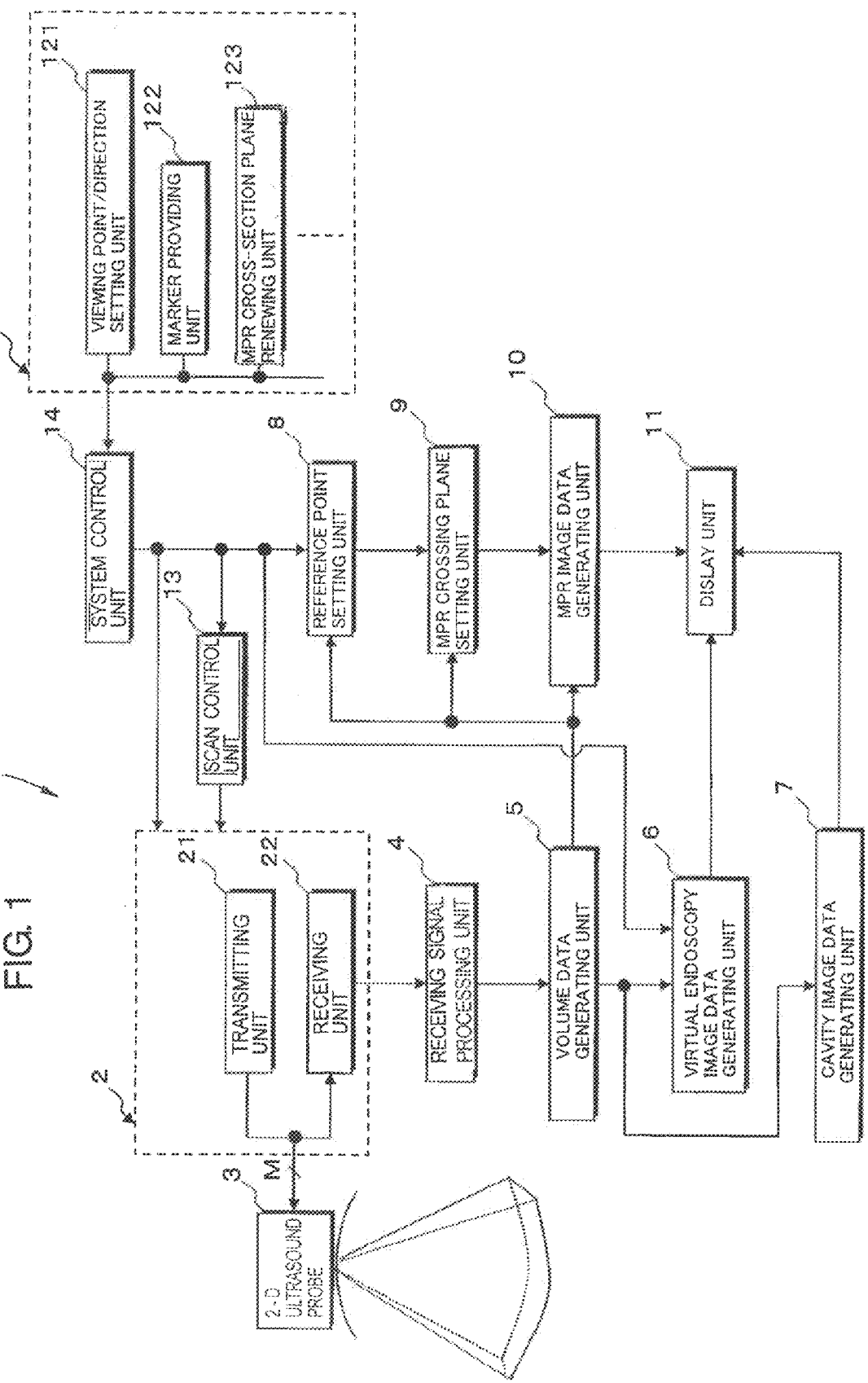
FIG. 1 is a block diagram illustrating an ultrasound diagnosis apparatus in accordance with a preferred embodiment of the present invention.

FIG. 1 is a block diagram of an ultrasound diagnosis system 100 in accordance with a preferred embodiment of the present invention. The ultrasound diagnosis system 100 includes a transmission/reception unit 2, a 2-D ultrasound probe 3, a receiving signal processing unit 4 and a volume data generating unit 5. The transmission/reception unit 2 supplies driving signals to a plurality of selected transducers in the ultrasound probe 3 for transmitting ultrasound pulses onto an object along prescribed directions. Further, the transmission/reception unit 2 performs phase compensation and summation of the plurality channel of receiving signals acquired through the selected transducers. Thus, the 2-D ultrasound probe 3 transmits ultrasound pulses (transmission ultrasound) over a diagnosis target region in an object and converts ultrasound echo signals into electric signals (receiving signals). The receiving signal processing unit 4 generates ultrasound data (B mode data) by processing the receiving signals after arranging in phases and adding. The volume data generating unit 5 generates volume data by arranging the B mode data acquired through 3D scan on an object so as to correspond with the transmission and reception directions of ultrasounds.

The ultrasound diagnosis system 100 further includes a virtual endoscopy image data generating unit 6, a cavity image data generating unit 7, a reference point setting unit 8, an MPR cross-sectional plane setting unit 9 and an MPR image data generating unit 10. The virtual endoscopy image data generating unit 6 generates virtual endoscopy image data by performing a rendering process of volume data based on a viewing point and viewing direction data set through an input unit 12. The cavity image data generating unit 7 generates image data for displaying an inner side of a lumen organ, such as a blood vessel by performing inversion processes of the voxel values. Hereinafter, the inverted image data is referred to as "cavity image data". The reference point setting unit 8 sets a reference point on a diagnosing target region of the volume data based on position data of a marker supplied from the input unit 12. The MPR cross-sectional plane setting unit 9 sets three MPR cross-sectional planes that are mutually orthogonally crossing at the reference point. Further, the MPR cross-sectional plane setting unit 9 renews positions and directions of the MPR cross-sectional plane based on renewal instruction signals supplied from the input unit 12. The MPR image data generating unit 10 generates MPR image data by extracting each voxel of the volume data corresponded to the MPR cross-sectional planes.

The ultrasound diagnosis apparatus 100, as illustrated in FIG. 1, further includes a display unit 11, an input unit 12, a scan control unit 13 and a system control unit 14. The display unit 11 displays virtual endoscopy image data, cavity image data and MPR image data. The input unit 12 sets a viewing point and a viewing direction to the volume data. The input unit 12 further provides a marker to a diagnosing target region of the virtual endoscopy image data and performs a renewal of the MPR cross-sectional plane. The input unit 12 further inputs various command signals. The scan control unit 13 controls ultrasound transmissions and receptions to 3D region of an object. The system control unit 14 totally controls each unit in the ultrasound diagnosis apparatus 100.

The ultrasound probe 3 includes a plurality (M) of 2D arrayed transducers (not shown) in a tip portion of the probe for transmitting ultrasound pulses (transmission ultrasound) over a 3D volume of a diagnosis object portion in an object. Ultrasound transmission and reception are performed by touching the tip portion of the probe to a body surface of an object. Thus, the plurality (M) of transducers is coupled to the transmission/reception unit 2 through a plurality channels (M) of a multi-core cable (not shown). In this embodiment, 2D array sector scanning ultrasound probe 3 is used for scanning ultrasound. Of course, it is possible to use another type of ultrasound probe, such as a linear scanning type ultrasound probe or a convex scan type ultrasound probe.

Figure 2:
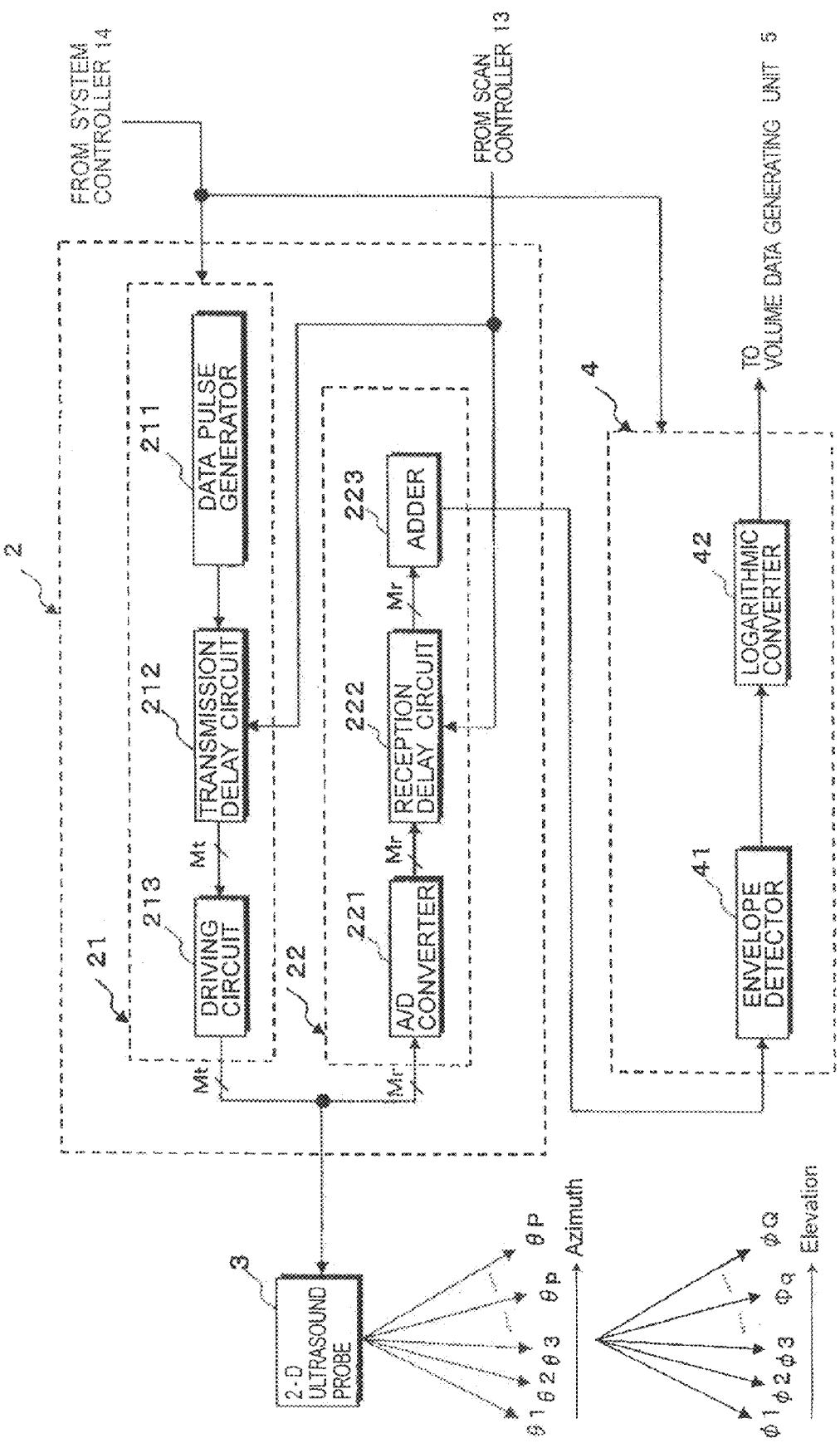
FIG. 2 is a block diagram illustrating the transmission and reception unit, and the receiving signal processing unit in the ultrasound diagnosis apparatus shown in FIG. 1.

FIG. 2 is a block diagram illustrating the transmission and reception unit 2 which includes a transmission unit 21 for driving a plurality (Mt) of transmission signals to the selected plurality (Mt) of transmitting transducers in the ultrasound probe 3 and a reception unit 22 for converting a plurality (Mr) of ultrasound echo signals supplied from the selected plurality (Mr) of receiving transducers. The transmission unit 21 includes a rate pulse generator 211, a transmission delay circuit 212 and a driving circuit 213. The rate pulse generator 211 generates rate pulses which determine a recycle period for transmission ultrasound. The generated rate pulses are supplied to the transmission delay circuit 212.

The transmission delay circuit 212 includes a plurality of independent delay circuits of the same number M of 2D array transducers as used for transmission in order to drive a selected number Mt among the plurality number (M) of transducers. The transmission delay circuit 212 gives a convergence delay time for converging the transmission ultrasound into a prescribed depth and a deviation delay time for transmitting ultrasound in a prescribed direction ($\theta xp$, $\theta yq$) to the rate pulses and supplies to the driving circuit 213. The driving circuit 213 drives the selected number Mt (Mt is equal or smaller than M) of transducers for transmitting ultrasound based on the rate pulses.

The reception unit 22 includes a plurality of A/D converters 221 corresponding to a plurality (Mr) of the selected receiving transducers, a plurality of reception delay circuits 222 for selected reception channels and a summation circuit 223 of 1 channel.

The reception delay circuit 222 gives each of the reception signals of Mr outputted from the A/D converter 221 a convergence delay time for converging reception ultrasound from a prescribed depth and a deviation delay time for setting reception directivity to a predetermined direction ($\theta xp$, $\theta yq$). The reception signals acquired from the prescribed direction ($\theta xp$, $\theta yq$) are added in the summation circuit 223. The delay time of the reception delay circuit 222 is controlled by the scan control unit 12.

It is possible for the reception unit 22 to simultaneously receive reception ultrasound beams from a plurality of directions by controlling the reception delay circuit 222 of Mr channels supplied from the transducers. By applying this parallel simultaneously reception, it becomes possible to significantly decrease the necessary time for performing a triggered entire volume mode scan.

Figure 3A:
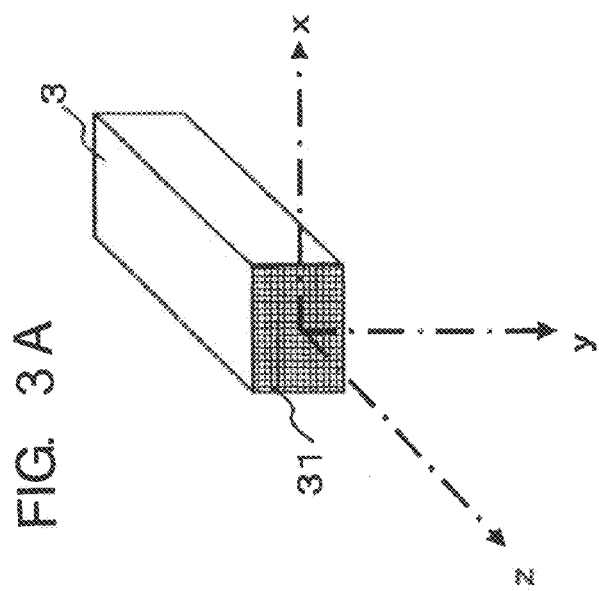
FIG. 3A illustrates the direction of ultrasound transmission and reception in a 3D (volume) scan by 2D array transducers provided in an ultrasound probe.
Figure 3B:
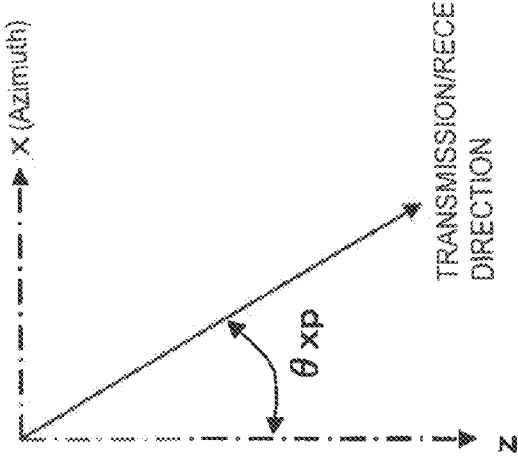
FIG. 3B illustrates the direction of ultrasound transmission and reception projected on the x-z plane in the volume scan shown in FIG. 3A.
Figure 3C:
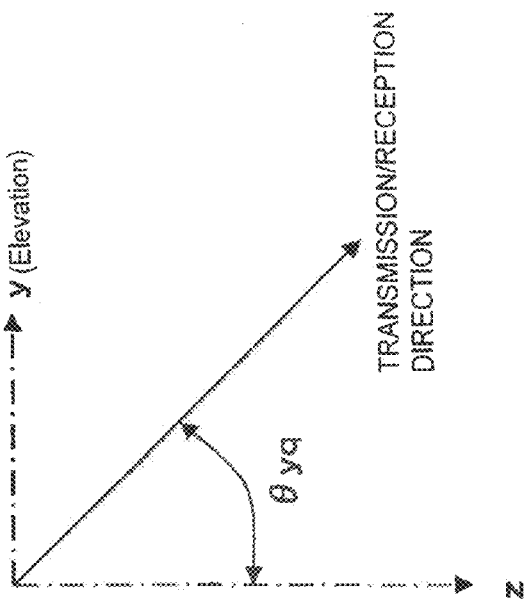
FIG. 3C illustrates the direction of ultrasound transmission and reception projected on the y-z plane in the volume scan shown in FIG. 3A.

FIG. 3A illustrates an ultrasound probe 3 having 2D array transducers Trs 31 and an ultrasound transmission/reception position P (r, $\theta xp$, $\theta yq$). The ultrasound probe 3 has a center axis (z-axis). The ultrasound transmission/reception position P (r, $\theta xp$, $\theta yq$) locates at a distance r from a surface of the transducers Trs in an x-axis (azimuth) direction and a y-axis (elevation) direction. FIG. 3B illustrates a projected position P on an x-z plane transmitting and receiving ultrasound at an angle $\theta xp$ in the x-axis (azimuth) direction from the z-axis. FIG. 3C illustrates a projected position P on a y-z plane transmitting and receiving ultrasound at an angle $\theta yq$ in the y-axis (elevation) direction from the z-axis. The delay time in the transmission delay circuit 212 in the transmission unit 21 and the reception delay circuit 222 in the reception unit 22 are controlled by the scan control signals supplied from the scan control unit 13 in order to perform a volume scan on a 3D region including a diagnosing target region of an object.

In FIG. 2, the reception signals processing unit 4 generates B mode data by processing the reception signals received from the reception unit 22. The reception signals processing unit 4 includes an envelope detector 41 for detecting the envelope of the reception signals supplied from the summation circuit 223 in the reception unit 22 and a logarithmic converter 42 for generating B mode data by converting the amplitude of the envelope detected reception signals. It is possible to replace of the positions of the envelope detector 41 and the logarithmic converter 42.

Figure 4:
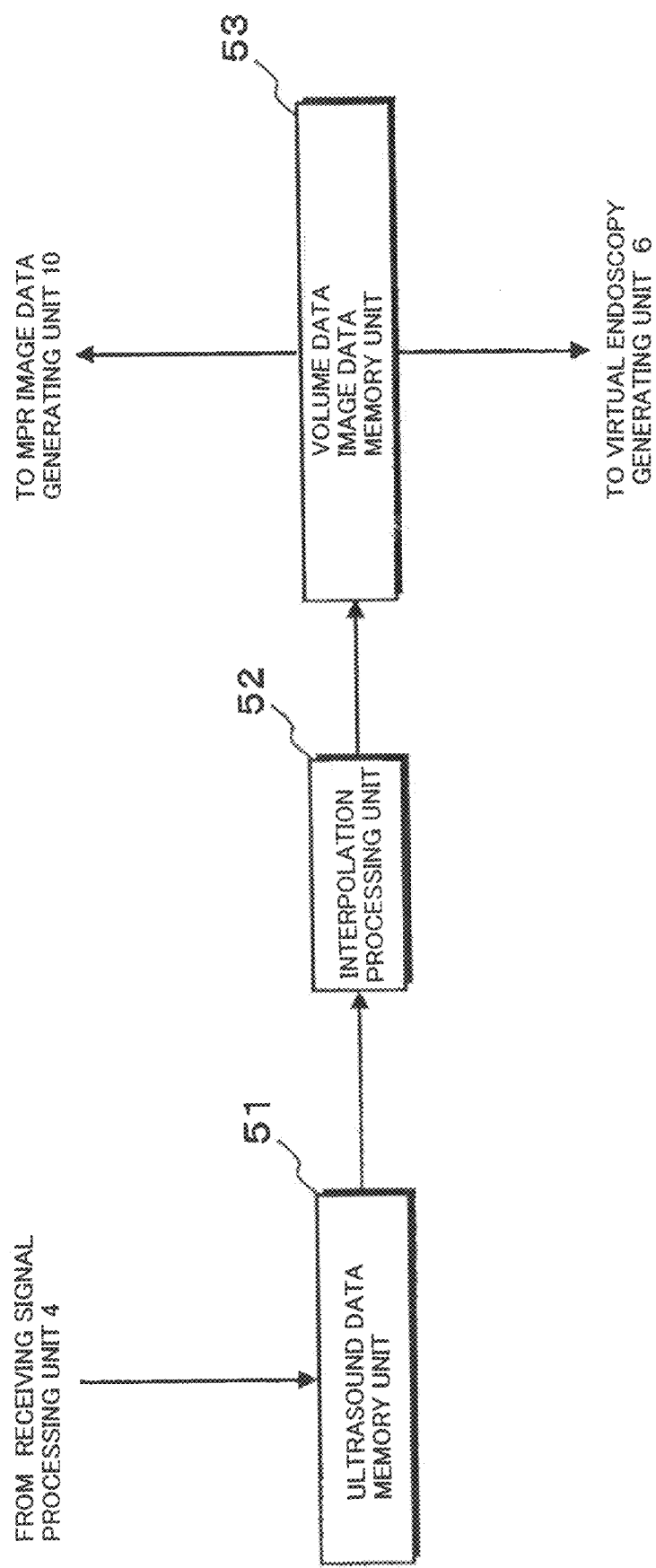
FIG. 4 is a block diagram illustrating the volume data generating unit in the ultrasound diagnosis apparatus shown in FIG. 1.

FIG. 4 illustrates a construction of the volume data generating unit 5 shown in FIG. 1. The volume data generating unit 5 includes an ultrasound data memory unit 51, an interpolation processing unit 52 and a volume data memory unit 53. However, it is possible to eliminate the interpolation processing unit 52. The ultrasound data memory unit 51 stores a plurality of ultrasound data generated in the reception signals processing unit 4 based on reception signals collected by a 3D scan on each of the plurality of 3D regions that are set on a diagnosis object portion in an object with accompanying of ultrasound transmission/reception directions. The interpolation processing unit in the sub-volume data generating unit 6 forms 3D ultrasound data by arranging the plurality of B mode data of 3D regions at a prescribed time phase that are read out from the B mode data memory unit in accordance with the transmission/reception directions ($\theta xp, \theta yq$). The interpolation processing unit 52 further generates 3D ultrasound data (volume data) formed of equidistant distance voxels by interpolating unequal distance voxels constructing the 3D ultrasound data. As explained above, it is possible to directly generate the volume data without performing interpolations. The acquired volume data are stored in the volume data memory unit 53.

In FIG. 1, the virtual endoscopy image data generating unit 6 includes an arithmetic circuit and a memory circuit (both not shown). In the memory circuit, an arithmetic processing program is preliminarily stored for generating virtual endoscopy image data by using volume data. The arithmetic circuit reads volume data stored in the memory circuit and the arithmetic processing program stored in the memory unit 53 in the volume data generating unit 5 for generating virtual endoscopy image data by performing a rendering process based on viewing point data and viewing direction data supplied from the input unit 12 through the system control unit 14.

Figure 5:
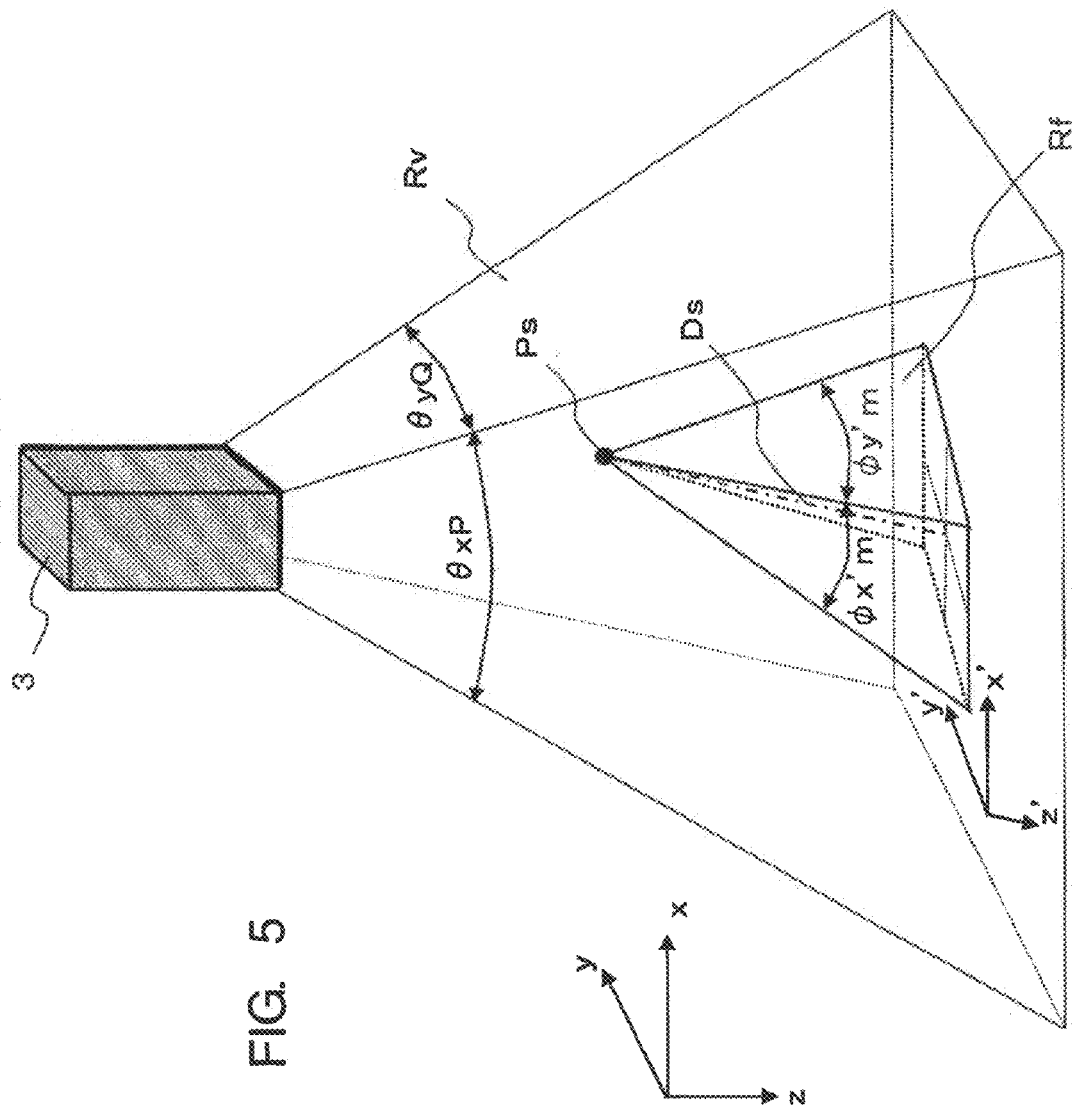
FIG. 5 illustrates a volume data generating region in an embodiment consistent with the present invention.

FIG. 5 illustrates a volume data generating region Rv generated in the volume data generating unit 5 and a virtual endoscopy image data generating region Rf set in the volume data generating region Rv. For instance, a viewing point Ps and a viewing direction Ds are set in a lumen of a follow organ volume data of an object generated in the volume data generating unit 5. The viewing direction Ds is starting from the viewing point Ps. Further, a viewing scope $\phi x'm$ along an x' direction and a viewing scope $\phi y'm$ along a y' direction are set centered on the viewing direction Ds. The arithmetic circuit in the virtual endoscopy image data generating unit 6 extracts volume data of the virtual endoscopy image data generating region Rf included in the viewing scopes $\phi x'm$ and $\phi y'm$ set in the volume data generating region Rv. The arithmetic circuit further generates virtual endoscopy image data by performing a rendering process of the acquired volume data based on the viewing point Ps and viewing direction Ds.

It is possible to freely set the orthogonal crossing coordinate system [x',y',z'] in the mutually orthogonal crossing coordinate system [x, y, z] for forming the volume data generating region Rv. In the coordinate system [x',y',z'], the z'-axis is formed in the viewing direction Ds for forming virtual endoscopy image data generating region Rf. It is also possible to set the viewing point Ps and viewing direction Ds under an observation of MPR image data generated by using volume data of the volume data generating region Rv. By successively renewing the position and direction of the viewing point Ps and viewing direction Ds provided to the volume data and by observing each acquired virtual endoscopy image data, it becomes possible to set a suitable viewing point Ps and viewing direction Ds.

The cavity image data generating unit 7 (FIG. 1) generates 3D cavity image data for displaying a lumen inside of a thin follow organ that has extremely small amplitude of ultrasound echo wave by performing a prescribed process of volume data generated in the volume data generating unit 5. Practically, an inversion process is performed for volume data that is inverted magnitude relations of the voxel values.

In FIG. 1, the input unit 12 provides a marker to a diagnosing target region of virtual endoscopy image data displayed on the display unit 11 for setting a viewing direction data. The reference line setting unit 8 receives via the system control unit 14 the observing direction data for setting a reference line having a starting point at the viewing point on the volume data for a generation of virtual endoscopy image data in the viewing direction.

By comparing between a voxel value of the volume data that is crossing the reference line and a prescribed threshold value $\alpha$ of the voxel value, a reference point is set to the volume data. Thus, an inner surface of diagnosing target region of a follow organ displayed by the virtual endoscopy image data and the reference line cross at the reference point. In this case, the amplitude of ultrasound echo wave acquired from the inner surface of the follow organs is usually larger than amplitudes of ultrasound echo wave acquired from another region. Accordingly, it becomes possible to set a reference point that indicates a crossing point between the reference line and the inner surface of the follow organ by measuring voxel values of volume data existed along the reference line.

Figure 6:
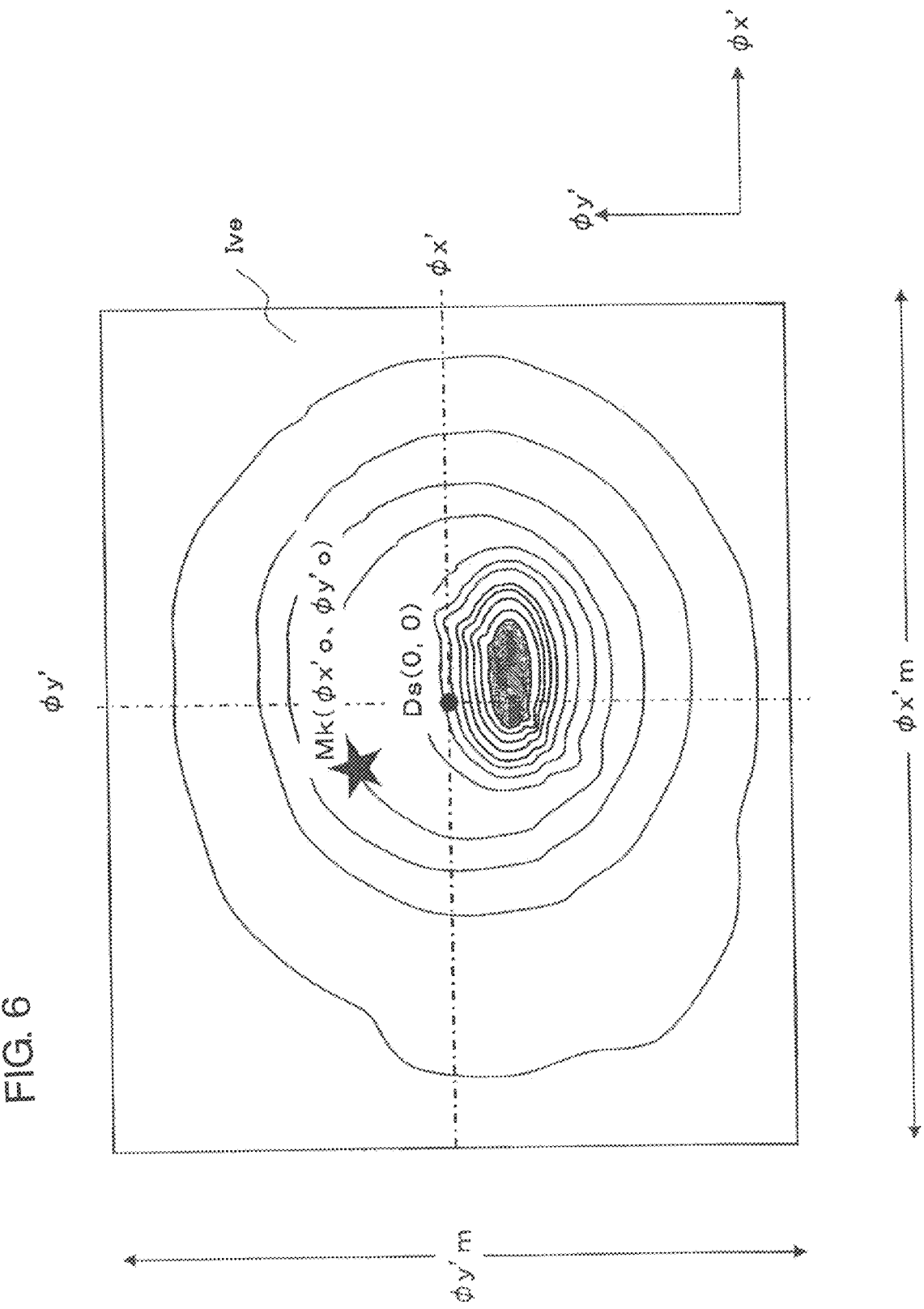
FIG. 6 illustrates a marker provided on a diagnosing target region of a virtual endoscopy image data according to a preferred embodiment consistent with the present invention.

FIG. 6 illustrates a marker arranged on a diagnosing target region of virtual endoscopy image data. Thus, the input unit 12 arranges the marker Mk on a diagnosing target region (not shown) that is shown by the virtual endoscopy image data generating region Rf (FIG. 5) a virtual endoscopy image data Iye of the virtual endoscopy image data generating region Rf (FIG. 5) surrounded by the viewing scope $\phi x'm$ along the x' direction and the viewing scope $\phi y'm$ along the y' direction that are centered at the viewing direction Ds and shown along the observing direction ($\phi x'o, \phi y'o$) of the virtual endoscopy image data Iye. Pixels of virtual endoscopy image data Iye at a position ($\phi x', \phi y'$) are formed based on the voxels of the volume data existed along the observing direction ($\phi x', \phi y'$). An azimuth axis and an elevation axis of the pixel correspond to $\phi x'$ and $\phi y'$, respectively.

Figure 7:
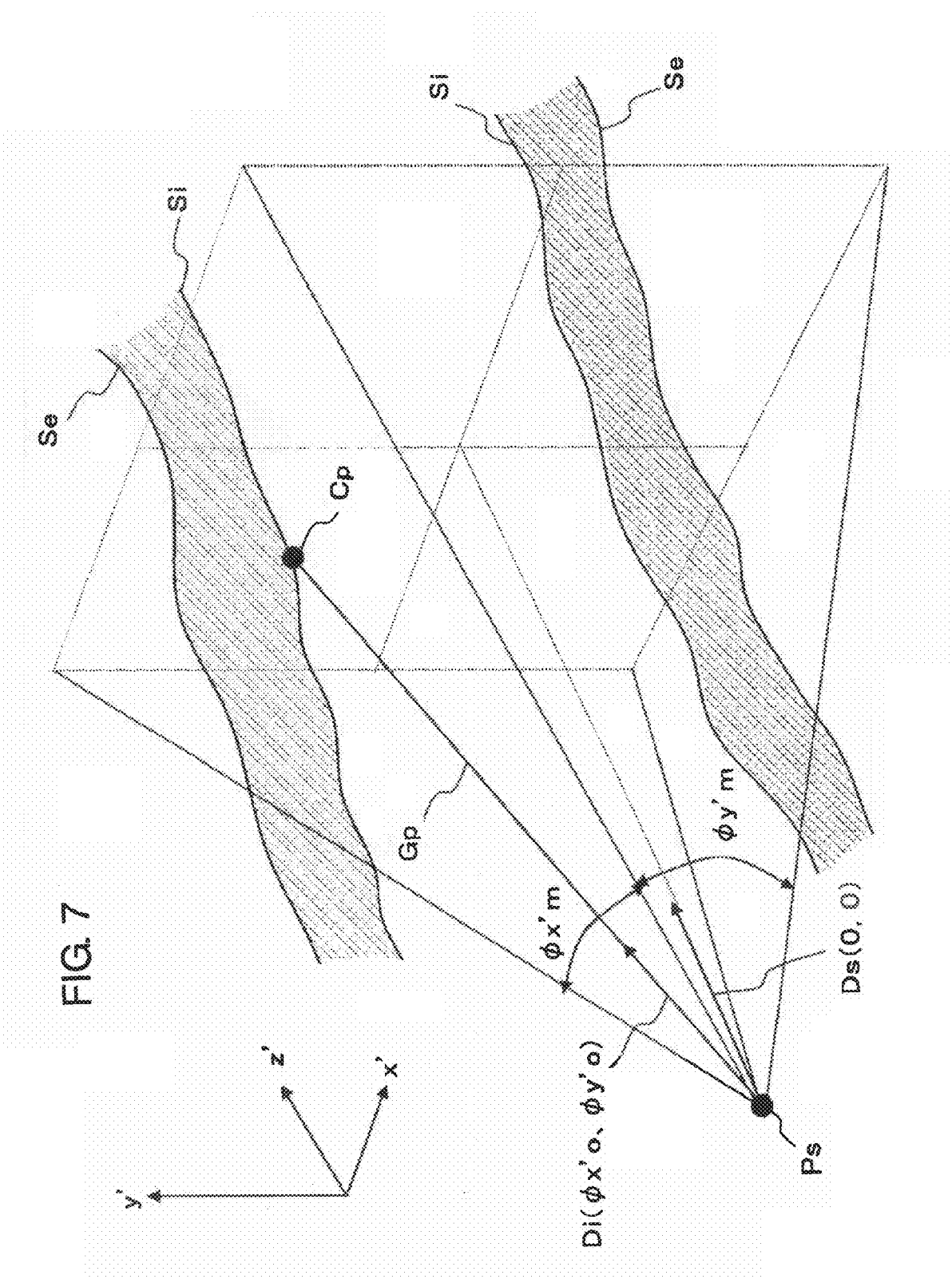
FIG. 7 illustrates a reference line set on a volume data of a preferred embodiment consistent with the present invention and a reference point where the reference line is crossing on an inner surface of a diagnosing target region of a follow organ.

FIG. 7 illustrates a reference line Gp and a reference point Cp that are set up to acquire virtual endoscopy image data of a follow organ (lumen). The reference line Gp indicates an observing direction ($\phi x'o, \phi y'o$) set up on the volume data of the virtual endoscopy image data generating region Rf. The reference point Cp indicates a crossing point at which the reference line Gp along the observing direction ($\phi x'o, \phi y'o$) and the follow organ inner surface Si along the reference line Gp are crossing over. As illustrated in FIG. 7, to acquire virtual endoscopy image data of a follow organ (lumen) that is surrounded by the inner surface Si, a viewing point Ps is set up at a position in the inner surface Si of the follow organ. Then, a reference line Gp started from the viewing point Ps is set up along the observing direction ($\phi x'o, \phi y'o$).

Referring to FIG. 1, the MPR cross-sectional planes setting unit 9 sets up three MPR cross-sectional planes that are mutually orthogonally crossing at the reference point Cp. Further, the MPR cross-sectional planes setting unit 9 renews positions and directions of the MPR cross-sectional plane based on a renewal instruction signal supplied from the input unit 12.

Figure 8:
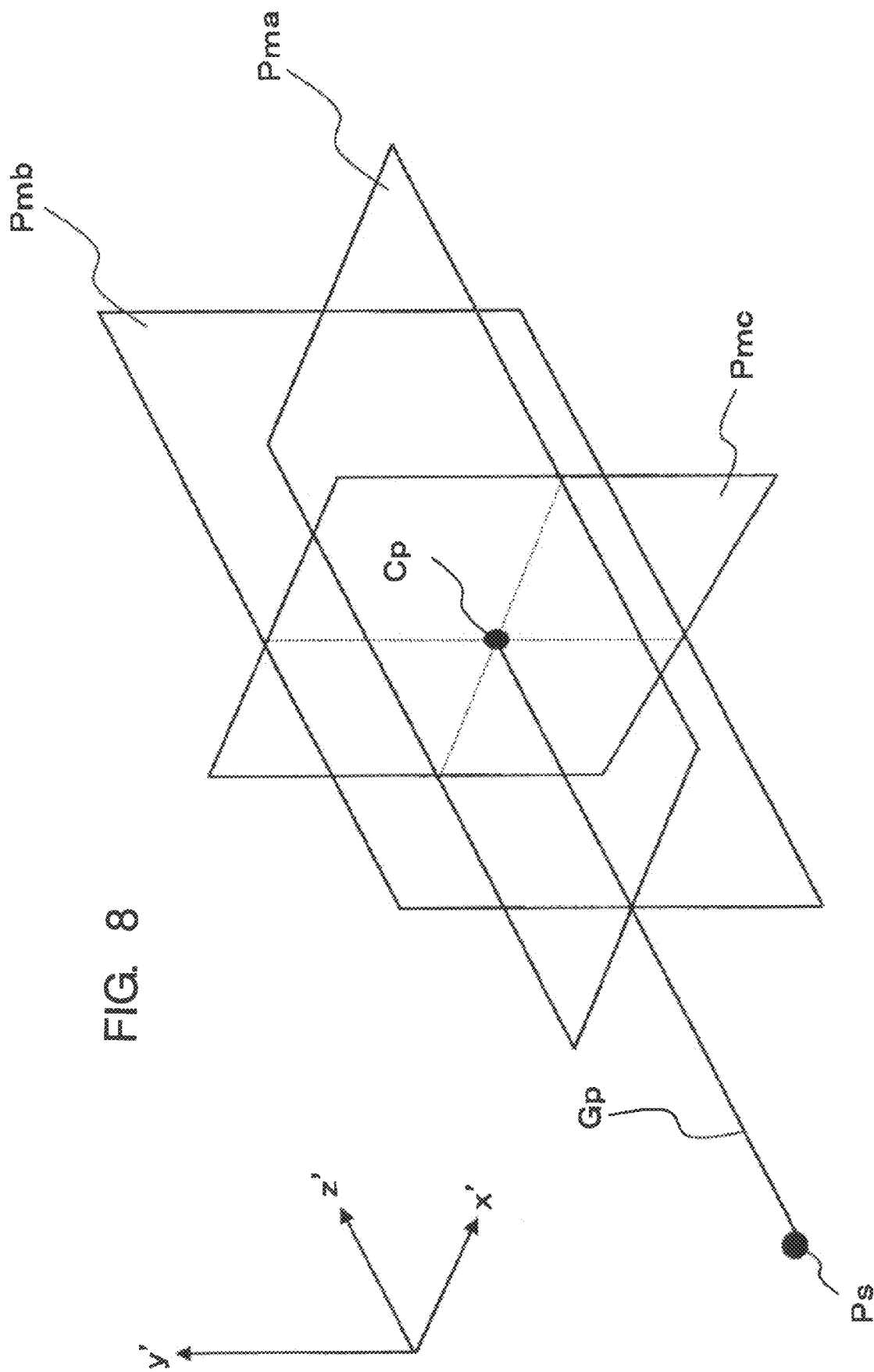
FIG. 8 illustrates an MPR cross-sectional plane set by the MPR cross-sectional plane setting unit in the preferred embodiment consistent with the present invention.

FIG. 8 illustrates the MPR cross-sectional planes set up by the MPR cross-sectional planes setting unit 9. For instance, three MPR cross-sectional planes are set up based on the orthogonally crossing coordinate system [x', y', z'] of the virtual endoscopy image data generating region Rf shown in FIG. 5. As illustrated in FIG. 8, the MPR cross-sectional planes set up an MPR cross-sectional plane Pma that is parallel to a (x'-z') plane including the reference point Cp set up by the reference point setting unit 8, an MPR cross-sectional plane Pmb parallel to a (y'-z') plane and an MPR cross-sectional plane Pmc parallel to a (x'-y') plane. By supplying a renewal instruction signal from the input unit 12 through the system control unit 14, these three orthogonal MPR cross-sectional planes can be moved to a desired position along a desired direction while keeping the relative position relationships.

The MPR image data generating unit 10 (FIG. 1) reads out volume data stored in the volume data memory unit 53 of the volume data generating unit 5. Three MPR image data Ima to Imc are generated by setting up the MPR cross-sectional planes Pma to Pmc to the volume data. Practically, each of MPR image data Ima to Imc is generated based on the respective volume data corresponding to each of MPR cross-sectional planes Pma to Pmc.

The display unit 11 (FIG. 1) includes a display data generating unit, a data conversion unit and a monitor (all not shown). The display data generating unit in the display unit 11 selects a desired image data among the virtual endoscopy image data Ive generated in the virtual endoscopy image data generating unit 6, MPR image data Pma to Pmc generated in the MPR image data generating unit 10 and cavity image data generated in the cavity image data generating unit 7 based on a display data selection signal supplied from input unit 12, and generates display data with attaching collateral data, such as an object data to the desired image data. The data conversion unit in the display unit 11 displays the display data generated by the display data generating unit on a monitor by performing conversion processes, such a display format conversion and a D/A conversion.

FIGS. 9A-9D and 10A-10D illustrate specific examples of display data displayed on a monitor. FIG. 9A illustrates MPR image data Ima of a diagnosing target region of a blood vessel generated on the MPR cross-sectional plane Pma shown in FIG. 8. FIG. 9B shows MPR image data Imb generated on the MPR cross-sectional plane Pmb depicted in FIG. 8. FIG. 9C illustrates MPR image data Imc of a cross-sectional view of the blood vessel along a normal line (N.L) to a surface of the blood vessel from the reference point Cp shown in FIG. 9B. FIG. 9D illustrates virtual endoscopy image data Ive showing an inner surface a blood vessel.

In each of the MPR image data Ima, Imb and Imc acquired on the respective MPR cross-sectional planes, a reference point Cp that indicates a crossing point between an inner surface of a diagnosing target region in the lumen organ (blood vessel) Ov and the reference line along an observing direction ($\phi$x'o, $\phi$y'o) and another two MPR cross-sectional planes including the reference point Cp are displayed as display data. For instance, MPR image data Ima (FIG. 9A) acquired on MPR cross-sectional plane Pma shows the reference point Cp and another two MPR cross-sectional planes Pmb and Pmc which include the reference point Cp. In the virtual endoscopy image data Ive shown by FIG. 9D, the reference point Cp is illustrated in the diagnosing target region in the follow organs Ov.

When the reference point Cp shown in either one of the four image data Ima, Imb, Imc or Imv is moved to a desired direction by using an input device provided in the input unit 12, the reference point Cp shown in another three image data are also moved in conjunction with the moving indicated reference point Cp. After moving, three MPR cross-sectional planes are set up by including the moved reference point Cp. Each of the MPR image data Ima to Imc shown in FIGS. 9A to 9C are respectively renewed by MPR image data generated on the newly set up MPR cross-sectional planes.

FIG. 10A illustrates the MPR image data Ima generated on the MPR cross-sectional plane Pma as similar as illustrated in FIG. 9A. FIG. 10B illustrates the cavity image data Icy of the blood vessel shown in FIG. 10A. FIG. 10C illustrates an MPR image data Imc of a cross-sectional view of the blood vessel along a normal line to a surface of the blood vessel from the reference point Cp on the cavity image shown in FIG. 10B. FIG. 10D illustrates the virtual endoscopy image data Ive of the blood vessel. In the cavity image data Icy shown in FIG. 10B, a reference point Cp that indicates a cross point between an inner surface of a diagnosing target region of the lumen organ Ov and a reference line along the observing direction ($\phi$x'o, $\phi$y'o) is appended. FIG. 10C is a cross-sectional view of a blood vessel along a normal line (N.L.) from the reference point Cp located on an inner surface of the cavity image shown in FIG. 10B.

When the reference point Cp shown in either one of the image data is moved to a desired direction by an instruction from the input unit 12, the reference point Cp shown in other image data are also moved in conjunction with the moving of the indicated reference point Cp, and MPR image data Ima shown in FIG. 10A and MPR image data Imc shown in FIG. 10C are renewed by the MPR image data newly generated by the newly set up MPR cross-sectional planes including the moved reference point Cp.

In FIG. 1, the input unit 12 includes input devices such as a display panel, a key board, and pointing devices, such as a trackball, a mouse, selection buttons or input buttons. The input unit 12 further includes a viewing point/viewing direction setting unit 121 for setting a viewing point and a viewing direction to the volume data, a marker providing unit 122 for providing a marker on a diagnosing target region of the virtual endoscopy image data and an MPR cross-sectional plane renewing unit 123 for renewing the position or the direction of the MPR cross-sectional plane. By using the display panel or the input devices, an object data and various command signals are inputted, a volume data generating condition, a virtual endoscopy image data generating condition and an MPR image data generating conditions, a threshold value $\alpha$ and viewing scopes $\phi$x'm and $\phi$y'm are set up and display data is selected.

The scan control unit 13 (FIG. 1) controls delay times of the transmission delay circuit 212 in the transmitting unit 21 and the reception delay circuit 222 (FIG. 2) in the receiving unit 22 for successively performing ultrasound transmissions/receptions to 3D regions on an object.

The system control unit 14 includes a CPU and a memory circuit (both not shown). The memory circuit in the system control unit 14 stores various data inputted, set up or selected by the input unit 12. The CPU in the system control unit 14 totally controls each unit in the ultrasound image diagnosis apparatus, and generates and displays virtual endoscopy image data, cavity image data and MPR image data. It is also possible to use GPU or ASIC by replacing CPU.

Figure 11:
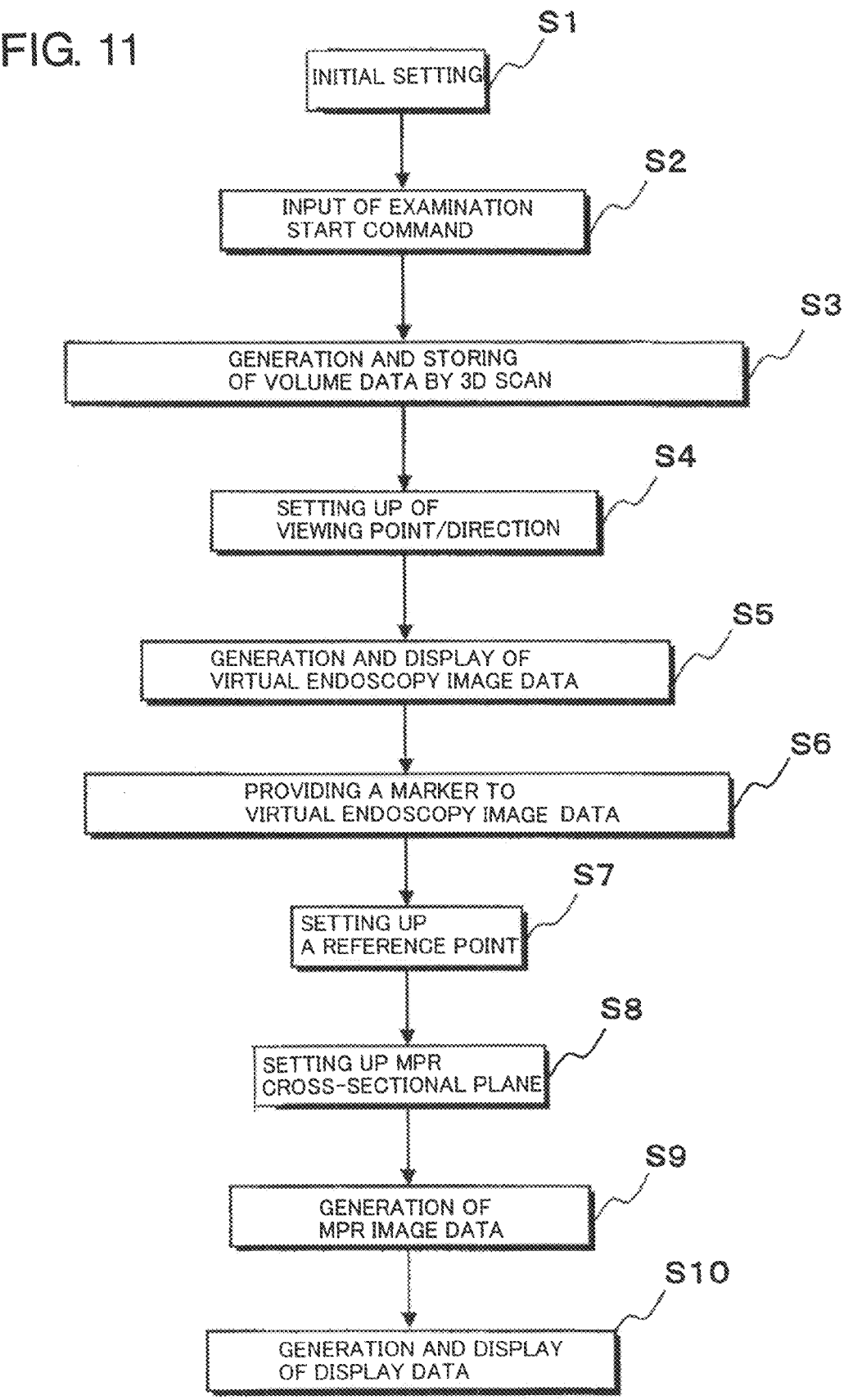
FIG. 11 is a flowchart illustrating an embodiment of a medical image displaying method consistent with the present invention.

FIG. 11 is a flowchart for illustrating an embodiment of the medical image displaying method consistent with the present invention. Prior to start an ultrasound examination for an object, an operator of the ultrasound diagnosis apparatus 100 inputs the object data and sets up operations, such as generating conditions of a volume data, virtual endoscopy image data, MPR image data, the threshold value $\alpha$ for detecting voxels and viewing scopes $\phi$x'm and $\phi$y'm. The operator further selects display data by using the input unit 12. Then, the operator performs an initial setting of an ultrasound probe 3 at an appropriate position on a body surface of the object (FIG. 11, step S1). In this embodiment, display data is generated by composing the virtual endoscopy image data selected based on the selection signal and MPR image data under the display format illustrated in FIG. 9. Of course, as illustrated in FIG. 10, it is possible to generate the display data by composing the virtual endoscopy image data, the cavity image data and the MPR image data.

After completing the initial settings, the operator inputs an examination start command through the input unit 12 (FIG. 11, step S2). This command signal is supplied to the system control unit 14 for starting acquisition of volume data of a 3D region in an object. Thus, as illustrated in FIG. 2, the rate pulse generator 211 in the transmitting unit 21 generates rate pulses by dividing the reference signal supplied from the system control unit 14 and supplies rate pulses to the transmission delay circuit 212. The transmission delay circuit 212 gives a focusing delay time for focusing transmitted ultrasounds a prescribed depth and a deflection delay time for emitting the transmitted ultrasounds along the first transmission/reception direction ($\theta x1$, $\theta y1$) at the rate pulse based on the control signals supplied from the transmission/reception control unit 11.

Based on the rate pulses supplied from the transmission delay circuit 212, the driving circuit 213 generates driving signals for driving a plurality (Mt) of transmission transducers in the ultrasound probe 3 for transmitting ultrasounds onto the object.

A portion of the transmitted ultrasounds reflect at boundary surfaces of an organ or tissues having different acoustic impedances in the object. The reflected ultrasounds are received through a plurality (Mr) of transducers in the ultrasound probe 3 and converted to reception signals of Mr channels. The Mr channels reception signals supplied from the transducers in the ultrasound probe 2 are converted to digital signals through the A/D converter 221. Further, the reception delay circuits 222 of Mr channels gives the focusing delay times for focusing the Mr channels reception signals from a prescribed depth and the deflecting delay time for setting a strong reception directivity to the transmission/reception direction ($\theta x1, \theta y1$). The focused Mr channels reception signals are phase compensated and summed at the summation unit (adder) 223.

The phase compensated and summed receiving signals are supplied to the receiving signal processing unit 4. The receiving signal processing unit 4 generates B mode ultrasound data by performing envelope detections and logarithmic conversions. The generated B mode data is stored in the ultrasound data memory unit 51 of the volume data generating unit 5 with the transmission/reception direction ($\theta x1, \theta y1$) attached as appendix data.

After finishing the generation and storing of the ultrasound data along the transmission/reception direction ($\theta x1, \theta y1$), the system control unit 14 performs 3D scan by successively renewing the transmission/reception directions ($\theta xp, \theta yq$) without the first transmission/reception direction ($\theta x1, \theta y1$). Thus, by controlling the delay times of the transmission delay circuit 212 in the transmission unit 21 and the reception delay circuit 222 in the reception unit 22, the transmission/reception directions ($\theta xp, \theta yq$) are successively renewed along the $\theta x$ direction by $\Delta \theta x$, and also renewed along the $\theta y$ direction by $\Delta \theta y$. Where $\theta xp = \theta x1 + (p-1)\Delta \theta x$ (p=1 to P), $\theta yq = \theta y1 + (q-1)\Delta \theta y$ (q=1 to Q). These ultrasound data acquired along the renewed transmission/reception directions also are stored in the ultrasound data memory unit 51 with the respective transmission/reception direction data attached.

As illustrated in FIG. 4, the volume data generating unit 5 generates 3D ultrasound data by arranging a plurality of ultrasound data read out from the ultrasound data memory unit 51 so as to correspond to each of the transmission/reception directions ($\theta xp, \theta yq$), where $\theta xp = \theta x1 + (p-1)\Delta \theta x$ (p=1 to P); $\theta yq = \theta y1 + (q-1)\Delta \theta y$ (q=1 to Q). The generated volume data is stored in the volume data memory unit 53 (FIG. 11, step S3).

Then, the operator tentatively sets up a viewing point and a viewing direction to volume data through the input unit 12 (FIG. 11, step S4). The virtual endoscopy image data generating unit 6 generates virtual endoscopy (fly-through) image data by performing a rendering process of volume data read out from the volume data memory unit 53 in the volume data generating unit 5 based on the viewing point and viewing direction data supplied from the input unit 12 through the system control unit 14 (FIG. 11, step S5). Under observation of the virtual endoscopy image data displayed on a monitor in the display unit 11, an appropriate viewing point and viewing direction for diagnosing target region is newly set up.

When a favorable acquisition of virtual endoscopy image data for the target region to be diagnosed is succeeded, the operator provides a marker on the diagnosing target region of the virtual endoscopy image data displayed on the display unit 11 by using input devices in the input unit 12 (FIG. 11, step S6).

Based on the observing direction data for the diagnosing target region set up by providing the marker on the virtual endoscopy image data, the reference point setting unit 8 sets up a reference line that originates from the viewing point. Further, by comparing a voxel value of the volume data at a crossing point to the reference line with a threshold value $\alpha$ for voxel detection, a reference point is set up to the volume data at a crossing point where an inner surface of the diagnosing target region of the follow organ displayed by the virtual endoscopy image data the reference line is crossing with the reference point (FIG. 11, step S7).

Then, the MPR cross-sectional plane setting unit 9 sets up three MPR cross-sectional planes that are mutually orthogonally crossing at the reference point (FIG. 11, step S8). The MPR image data generating unit 10 sets up the MPR cross-sectional planes on the volume data read out from the volume data memory unit 53 in the volume data generating unit 5. By extracting each 3D ultrasound data corresponding to each of the MPR cross-sectional planes, 2D MPR image data is generated (FIG. 11, step S9).

When the generation of MPR image data has completed, the display unit 11 composes the virtual endoscopy image data generated in the virtual endoscopy image data generating unit 6 and the three MPR image data generated in the MPR image data generating unit 10. Further, the display unit 11 displays the generated display data with attached appendix data of the object data on the monitor (FIG. 11, step S10).

If it is desired to observe these various image data with a different viewing scope or at different MPR cross-sectional planes, the generation and display of the virtual endoscopy image data and the MPR image data are similarly repeated. For instance, by moving the reference point attached to the MPR image data displayed on the monitor in the display unit 11 by using an input device in the input unit 12, it becomes possible to generate MPR image data on a desired MPR cross-sectional plane.

According to the above-explained embodiment and the modification, it becomes possible to simultaneously acquire virtual endoscopy image data and a plurality of MPR image data on a diagnosing target region based on the volume data acquired from an object. Consequently, it becomes possible to observe inner tissues by comparing organ surfaces of a diagnosing target region in a follow organ, which can significantly improve diagnosis accuracy and efficiency. In particular, by observing an organ surface status due to the virtual endoscopy image data, an inner surface of a follow organ to which it is difficult to insert an endoscope can easily be observed. Further, obtaining the volume data used for a generation of the virtual endoscopy image data eliminates invasion of the subject resulting in greatly reduced risk to the subject, since these data are acquired through an ultrasound probe provided outside of an object body.

Further, since the MPR cross-sectional planes are formed at a reference point set up on a diagnosing target region of volume data, and the position and the direction of the MPR cross-sectional plane can be automatically renewed in association with a renewal of the reference point by an input operation, it becomes always possible to observe a desired virtual endoscopy image with comparing to the MPR image. In particular, by setting up three MPR cross-sectional planes mutually orthogonally cross at the reference point, it can efficiently acquire detail data of inner tissues that are effective for a diagnosis of the diagnosing target region.

According to the above-explained embodiment and the modification of the ultrasound diagnosis apparatus, it is possible to determine accurately a positional relationship of a diagnosing target region to a follow organ (lumen) by comparatively displaying between the emphasized lumen cavity image data in a follow organ and the MPR image data.

Figure 12:
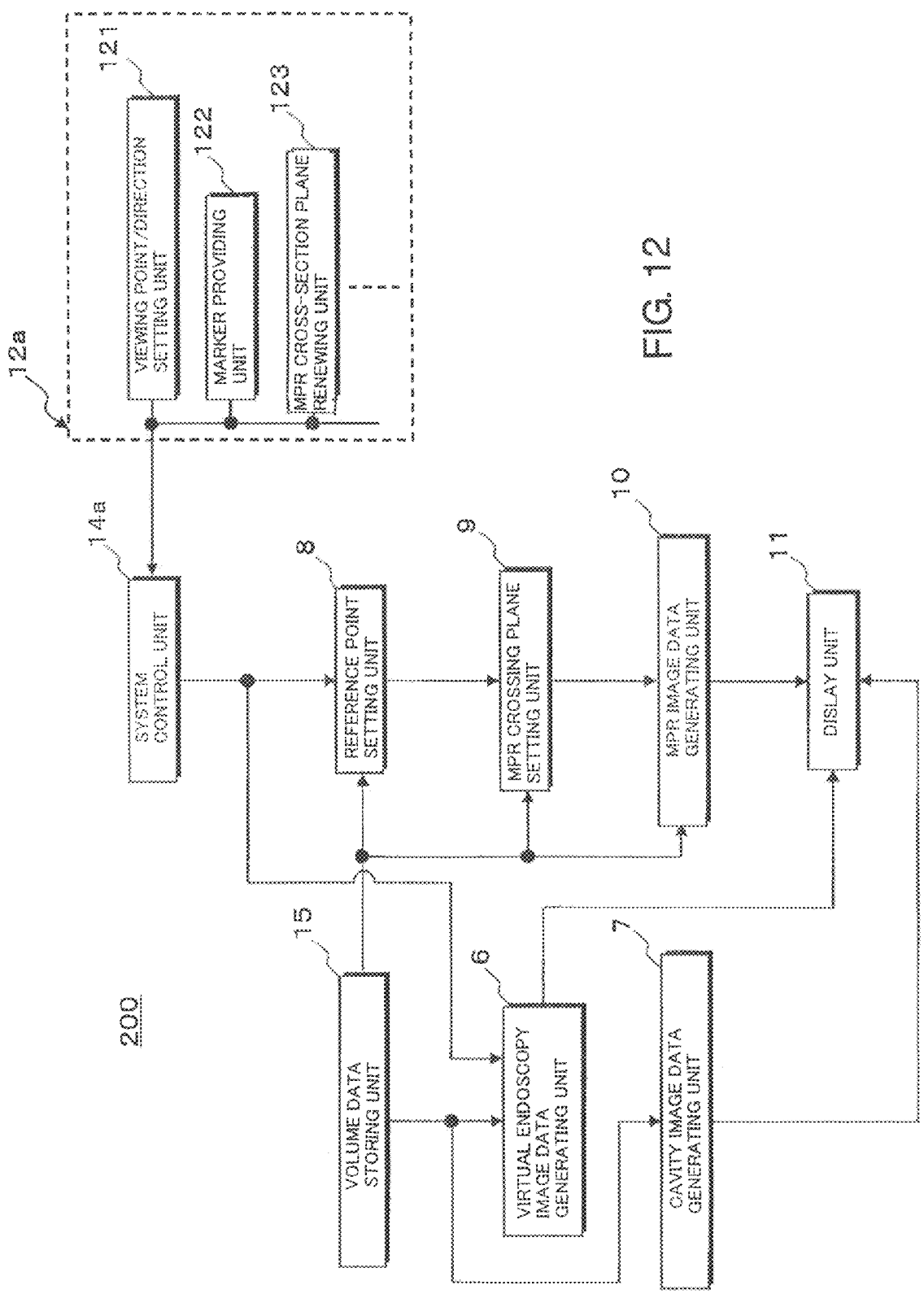
FIG. 12 is a block diagram illustrating the medical image display apparatus consistent with a preferred embodiment according to the present invention.

FIG. 12 explains an embodiment of a medical image display apparatus consistent with the present invention. The medical image display apparatus generates virtual endoscopy image data by setting up a viewing point and a viewing direction to an object volume data acquired through an ultrasound diagnosis apparatus. By providing a marker on a diagnosing target region of a follow organ displayed by the virtual endoscopy image data, an observing direction is set up. Then, a reference line originated from the viewing point is set up in the observing direction of the volume data used for a generation of the virtual endoscopy image data. By comparing a the volume data crossing the reference line and a prescribed threshold value, a reference point where a surface of a diagnosing target region displayed by the virtual endoscopy image data is crossing to the reference line is set up in the volume data. A plurality of MPR image data is generated by extracting the volume data corresponded to the respective three MPR cross-sectional planes that are mutually orthogonally crossing at the reference point, and these MPR image data are displayed with the virtual endoscopy image data.

FIG. 12 illustrates a construction of an embodiment of the medical image display apparatus 200 consistent with the present invention. To avoid redundant explanations, each unit that has the same construction and function as the units of the ultrasound diagnosis apparatus 100 shown in FIG. 1 is indicated by the same number.

The medical image display apparatus 200 includes a volume data storing unit 15, a virtual endoscopy image data generating unit 6, a cavity image data generating unit 7, a reference point setting unit 8, an MPR cross-sectional plane setting unit 9 and an MPR image data generating unit 10. The volume data storing unit 15 stores volume data of an object that is acquired by an ultrasound diagnosis apparatus. The virtual endoscopy image data generating unit 6 generates virtual endoscopy image data by performing a rendering process of the volume data based on a viewing point and a viewing direction set up by the input unit 12a. The cavity image data generating unit 7 generates cavity image data by performing an inversion process of a voxel value of the volume data. The reference point setting unit 8 sets up a reference point on a diagnosing target region of the volume data based on a position data of a marker supplied from the input unit 12a. The MPR cross-sectional plane setting unit 9 sets up three MPR cross-sectional planes that are mutually orthogonally crossing at the reference point. Further, the MPR cross-sectional plane setting unit 9 renews the positions and directions of the MPR cross-sectional planes based on renewal instruction signals supplied from the input unit 12a. The MPR image data generating unit 10 generates MPR image data by extracting voxel value of the volume data corresponded to each of the MPR cross-sectional planes.

The medical image display apparatus 200 further includes a display unit 11, an input unit 12a and a system control unit 14a. The display unit 11 displays virtual endoscopy image data, cavity image data and MPR image data. The input unit 12a sets up a viewing point and a viewing direction to the volume data, and provides a marker on a diagnosing target region of the virtual endoscopy image data. The input unit 12a further renews the MPR cross-sectional planes, and inputs various command signals. The system control unit 14a totally controls each unit in the medical image display apparatus 200.

As explained above, the input unit 12a includes input devices such as a display panel, a key board, pointing devices, such as a trackball, a mouse, selection buttons or input buttons. The input unit 12a includes a viewing point/viewing direction setting unit 121 for setting a viewing point and a viewing direction to the volume data, a marker providing unit 122 for providing a marker on a diagnosing target region of the virtual endoscopy image data, and an MPR cross-sectional plane renewing unit 123 for renewing the position or the direction of the MPR cross-sectional planes. Further, operations for setting up virtual endoscopy image data generating conditions, MPR image data generating conditions, a threshold value $\alpha$ and viewing scope $\phi x'm$ and $\phi y'm$, input operations for an object data and various command signals and a selecting operation of display data are performed by using the display panel or the input devices.

The system control unit 14a totally controls each unit in the medical image display apparatus 200 based on the inputted, set up or selected data for generating and displaying virtual endoscopy image data, cavity image data and MPR image data. In this embodiment, the various image data are generated and displayed by the similar generating and displaying processes as illustrated in FIG. 11, steps S4 to S10.

According to the medical image display apparatus consistent with the present invention, as similar to the above-mentioned ultrasound diagnosis apparatus, it becomes possible to simultaneously acquire virtual endoscopy image data and a plurality of MPR image data of a diagnosing target region based on the volume data acquired from an object. Consequently, it becomes possible to observe an organ surface of a diagnosing target region of a follow organ while comparing the internal tissues so as to significantly improve the accuracy and efficiency of the diagnosis.

MPR cross-sectional are formed at the reference point set up set in a diagnosing target region of the volume data, and the position and the direction of the MPR cross-sectional plane are automatically renewed in conjunction with a renewal of the reference point by an operator. Consequently, it becomes possible to always observe a desired virtual endoscopy image with comparison to MPR image. In particular, by setting three MPR cross-sectional planes that are mutually orthogonally crossing at the reference point, it can efficiently acquire inner tissues detail data that are useful for diagnosing a target region. Further, by displaying an emphasized cavity image data of an inner lumen organ with comparison to the virtual endoscopy image data and the MPR image data, it becomes possible to accurately determine a positional relationship of a diagnosing target region in a follow organ.

The medical image display apparatus consistent with the present invention can generate and display various image data by using volume data supplied from another provided medical image display apparatus through a network. Consequently, it becomes possible for an operator to efficiently examine the object and still avoid limits of specific times and places.

In the above-mentioned embodiment, to generate virtual endoscopy image data, a viewing point is set up in a lumen of follow organs, such as an alimentary canal or blood vessels. According to the present invention, an application of a diagnosing target region is not limited to the above-mentioned follow organs. For instance, it is applicable to examine the hepatic cancer based on virtual endoscopy image data and MPR image data by setting up the viewing point in an abdominal cavity.

In the above-mentioned ultrasound diagnosis apparatus embodiment consistent with the present invention, three MPR cross-sectional planes Pma to Pmc are formed at reference point set up on a diagnosing target region in the volume data so as to orthogonally cross with each others and each of MPR image data Ima to Imc is generated on the respective MPR cross-sectional planes. Of course, the number of the MPR cross-sectional planes is not limited to three (3). In the embodiment, the cavity image data for emphasized displaying of inner side of a follow organ (lumen) is displayed accompanied by virtual endoscopy image data and MPR image data. It is possible to comparatively display with virtual endoscopy image data or MPR image data.

In the above-mentioned embodiment of ultrasound diagnosis apparatus consistent with the present invention, volume data is generated based on 3D B mode data acquired through a 2D array ultrasound probe and virtual endoscopy image data and MPR image data are generated by using the volume data. As mentioned above, it is possible to generate volume data by mechanically moving by 1D array ultrasound probe. It is also possible to generate volume data another ultrasound data, such as color Doppler data.

If each sizes of these image data, positions and directions are inadequate for generating and displaying virtual endoscopy image data and MPR image data, the input unit 12 (12*a*) can newly generate a desired virtual endoscopy image data and a desired MPR image data by rotating the orthogonally crossing coordinate system [x',y',z'] or the MPR cross-sectional plane and renewals of the viewing field angles φx'm and φy'm.

Other embodiments consistent with the present invention will be apparent to those skilled in the art from consideration of the specification and practice of the present invention disclosed herein. It is intended that the specification and examples be considered as exemplary only, with the true scope and spirit of the present invention being indicated by the following claims.

What is claimed is:
1. An ultrasound diagnosis apparatus, comprising:
an ultrasound probe; and
a processor configured to
generate volume data including a structure in an object based on an output of the ultrasound probe,
set a viewing point and a viewing direction to the volume data,
generate virtual endoscopy image data of the structure from the volume data based on the viewing point and the viewing direction set to the volume data,
set a marker on the virtual endoscopy image data by input from an operator,
set a reference line passing the viewing point to the volume data based on a position of the marker on the virtual endoscopy image data,
determine a reference point in the volume data where the reference line and a surface of the structure cross,
set at least one multi-planar-reconstruction (MPR) cross-sectional plane to the volume data based on the reference point,
generate at least one MPR image data from the volume data, the MPR image data corresponding to the MPR cross-sectional plane, and
cause a display to display both the virtual endoscopy image data and the MPR image data.

2. The ultrasound diagnosis apparatus according to claim 1, wherein the processor determines the reference point on a surface of the structure in relation to where a voxel value of the volume data crosses the reference line with a prescribed threshold value.

3. The ultrasound diagnosis apparatus according to claim 1, wherein the processor determines the reference point on an inner surface of the structure in a follow organ in relation to where a value of the volume data crosses the reference line with a prescribed threshold value.

4. The ultrasound diagnosis apparatus according to claim 1, wherein the processor sets three MPR cross-sectional planes that are orthogonally crossing at the reference point with each other.

5. The ultrasound diagnosis apparatus according to claim 1, wherein the processor causes the display to display for comparison the virtual endoscopy image data and the MPR image data as moving in conjunction with a moving direction of the reference line.

6. The ultrasound diagnosis apparatus according to claim 1, wherein the processor is further configured to generate cavity image data by performing an inversion process for a voxel value of the volume data, and
cause the display to display for comparison the virtual endoscopy image data, the MPR image data and the cavity image data.

7. The ultrasound diagnosis apparatus according to claim 1, wherein the processor is further configured to renew a position of the set MPR cross-sectional plane or a direction of the set MPR cross-sectional plane by moving a respective reference point appended to the virtual endoscopy image data and the MPR image data displayed on the display.

8. The ultrasound diagnosis apparatus according to claim 1, wherein the processor renews a position of a respective reference line appended on another image data in conjunction with a movement of a respective reference line appended on either one of the virtual endoscopy image data displayed on the display or the MPR image data.

9. A medical image display apparatus configured to generate and display virtual endoscopy image data based on volume data acquired through 3D scans of a medical image diagnosis apparatus, the medical image display apparatus comprising:
a memory configured to store the volume data including a structure in an object;
a processor configured to
set a viewing point and a viewing direction to the volume data;

generate virtual endoscopy image data by processing the volume data based on the viewing point and the viewing direction;
set a marker on the virtual endoscopy image data by an input from an operator;
set a reference line passing the viewing point to the volume data based on a position of the marker on the virtual endoscopy image data;
determine a reference point in the volume data where the reference line and a surface of the structure cross;
set at least one MPR cross-sectional plane to the volume data based on the reference point;
generate MPR image data by processing the volume data, the MPR image data corresponding to the MPR cross-sectional plane; and
cause a display to display both the virtual endoscopy image data and the MPR image data.

10. A medical image displaying method configured to generate and display virtual endoscopy image data based on volume data acquired through 3D scans by using a medical image diagnosis apparatus, the medical image displaying method comprising:

storing the volume data including a structure in an object;
setting a viewing point and a viewing direction to the volume data;
generating virtual endoscopy image data by processing the volume data based on the viewing point and the viewing direction;
setting a marker on the virtual endoscopy image data by an input from an operator;
setting a reference line passing the viewing point to the volume data based on a position of the marker on the virtual endoscopy image data;
determining a reference point in the volume data where the reference line and a surface of the structure cross;
setting at least one MPR cross-sectional plane to the volume data based on the reference point;
generating MPR image data by processing the volume data, the MPR image data corresponding to the MPR cross-sectional plane; and
displaying both the virtual endoscopy image data and the MPR image data.

* * * * *